US010156961B1

(12) United States Patent
Marchant et al.

(10) Patent No.: US 10,156,961 B1
(45) Date of Patent: Dec. 18, 2018

(54) DYNAMICALLY BUILDING A VISUALIZATION FILTER

(71) Applicant: EMC Corporation, Hopkinton, MA (US)

(72) Inventors: Kendra Marchant, Arlington, MA (US); Scott E. Joyce, Foxboro, MA (US); Natalie Lee Chin Wong, Brookline, MA (US); Paul D. Tynan, Lexington, MA (US); Rhon L. Porter, South Grafton, MA (US)

(73) Assignee: EMC IP Holding Company LLC, Hopkinton, MA (US)

( * ) Notice: Subject to any disclaimer, the term of this patent is extended or adjusted under 35 U.S.C. 154(b) by 154 days.

(21) Appl. No.: 14/035,768

(22) Filed: Sep. 24, 2013

(51) Int. Cl.
*G06F 3/0482* (2013.01)
*G06F 19/26* (2011.01)
*G06F 17/30* (2006.01)
*G06F 19/00* (2018.01)

(52) U.S. Cl.
CPC ...... *G06F 3/0482* (2013.01); *G06F 17/30395* (2013.01); *G06F 17/30398* (2013.01); *G06F 17/30634* (2013.01); *G06F 17/30646* (2013.01); *G06F 17/30958* (2013.01); *G06F 19/26* (2013.01); *G06F 17/3064* (2013.01); *G06F 17/30448* (2013.01); *G06F 17/30451* (2013.01); *G06F 17/30516* (2013.01); *G06F 17/30643* (2013.01); *G06F 17/30961* (2013.01); *G06F 19/708* (2013.01)

(58) Field of Classification Search
CPC ........ G06F 17/30516; G06F 17/30958; G06F 17/30451; G06F 17/30646; G06F 3/0482; G06F 17/30961; G06F 17/30448; G06F 17/30634; G06F 19/26; G06F 19/708; G06F 17/30643; G06F 17/30395; G06F 17/30398; G06F 17/3064
See application file for complete search history.

(56) References Cited

U.S. PATENT DOCUMENTS

| | | | | | |
|---|---|---|---|---|---|
| 5,608,861 | A | * | 3/1997 | Mead | G06T 11/206 715/700 |
| 5,608,899 | A | * | 3/1997 | Li | G06F 17/30395 |
| 5,621,905 | A | * | 4/1997 | Jewson | G06F 3/0482 715/841 |
| 5,787,411 | A | * | 7/1998 | Groff | G06F 17/30398 |
| 5,963,938 | A | * | 10/1999 | Wilson | G06F 17/30637 |
| 6,014,661 | A | * | 1/2000 | Ahlberg | G06F 17/30572 |
| 6,279,016 | B1 | * | 8/2001 | De Vorchik | G06F 17/30395 707/999.004 |
| 6,366,926 | B1 | * | 4/2002 | Pohlmann | G06F 9/542 |
| 6,385,602 | B1 | * | 5/2002 | Tso | G06F 17/30696 |
| 6,507,836 | B1 | * | 1/2003 | Nose | G06F 17/30554 |
| 6,539,371 | B1 | * | 3/2003 | Bleizeffer | G06F 17/30306 |

(Continued)

OTHER PUBLICATIONS

Seth B. Horan, et al.; "Unified Initialization Utility"; U.S. Appl. No. 13/630,093, filed Sep. 28, 2012.

(Continued)

*Primary Examiner* — Justin R. Blaufeld
*Assistant Examiner* — Jennifer E Nichols
(74) *Attorney, Agent, or Firm* — BainwoodHuang

(57) ABSTRACT

Techniques for presenting a dynamic graphical user interface (GUI) for selecting multiple non-conflicting filters to be used to filter performance data for display in a visualization are provided.

8 Claims, 4 Drawing Sheets

(56) References Cited

U.S. PATENT DOCUMENTS

| | | | |
|---|---|---|---|
| 6,785,668 B1* | 8/2004 | Polo | G06F 17/30395 707/769 |
| 6,894,639 B1* | 5/2005 | Katz | G01S 7/417 342/159 |
| 7,519,585 B2* | 4/2009 | Kenney | G06F 17/30398 |
| 7,574,432 B1* | 8/2009 | De Bellis | G06F 17/30392 |
| 7,584,172 B2* | 9/2009 | Heuer | G06F 17/30398 |
| 8,131,743 B1 | 3/2012 | Joyce et al. | |
| 8,171,046 B1 | 5/2012 | Joyce et al. | |
| 8,196,047 B2* | 6/2012 | Fisher | G06F 11/324 715/734 |
| 8,255,914 B1 | 8/2012 | Joyce et al. | |
| 8,347,219 B1* | 1/2013 | Joyce | G06F 9/451 715/762 |
| 8,423,567 B1* | 4/2013 | Finneran | G06F 17/30395 707/756 |
| 8,504,589 B2* | 8/2013 | Cubranic | G06F 17/30477 707/791 |
| 8,504,684 B1 | 8/2013 | Ballantyne et al. | |
| 8,712,815 B1* | 4/2014 | Nichols | G06F 11/3409 705/7.11 |
| 8,872,849 B2* | 10/2014 | Zhao | G06F 17/30389 345/440 |
| 8,931,036 B1* | 1/2015 | Cherukumudi | G06F 21/6218 709/225 |
| 8,954,880 B1 | 2/2015 | Rabe et al. | |
| 9,195,374 B1* | 11/2015 | Meaney | G06F 3/0484 |
| 9,201,573 B1 | 12/2015 | Miles et al. | |
| 9,235,424 B1* | 1/2016 | Wong | G06Q 10/06 |
| 9,348,881 B1* | 5/2016 | Hao | G06Q 10/10 |
| 2002/0052984 A1* | 5/2002 | Jindal | G06F 9/465 719/330 |
| 2004/0189707 A1* | 9/2004 | Moore | G06F 17/30115 715/777 |
| 2004/0207666 A1* | 10/2004 | Hally | G06F 3/04842 715/854 |
| 2004/0230599 A1* | 11/2004 | Moore | G06F 3/0481 |
| 2005/0004911 A1* | 1/2005 | Goldberg | G06F 17/30398 |
| 2005/0071737 A1* | 3/2005 | Adendorff | G06Q 10/00 715/276 |
| 2005/0165841 A1* | 7/2005 | Kasperkiewicz | G06F 17/3028 |
| 2006/0074879 A1* | 4/2006 | Covington | G06F 17/30398 |
| 2006/0101013 A1* | 5/2006 | Kenney | G06F 17/30398 |
| 2006/0197762 A1* | 9/2006 | Smith | G06T 11/206 345/440 |
| 2007/0192712 A1* | 8/2007 | Lee | G06F 3/0236 715/764 |
| 2008/0104051 A1* | 5/2008 | Gosper | G06F 17/30643 |
| 2008/0104053 A1* | 5/2008 | Cubranic | G06F 17/30477 |
| 2008/0163085 A1* | 7/2008 | Subbu | G06F 9/451 715/763 |
| 2008/0195930 A1* | 8/2008 | Tolle | G06F 17/246 715/227 |
| 2008/0201313 A1* | 8/2008 | Dettinger | G06F 17/30392 |
| 2008/0307362 A1* | 12/2008 | Chaudhri | G06F 3/0481 715/835 |
| 2009/0007021 A1* | 1/2009 | Hayton | G06F 8/34 715/843 |
| 2009/0100086 A1* | 4/2009 | Durrant | G06T 11/206 |
| 2009/0125482 A1* | 5/2009 | Peregrine | G06F 17/30864 |
| 2009/0225082 A1* | 9/2009 | Hargrove | G06T 11/206 345/440 |
| 2009/0265370 A1* | 10/2009 | Rucker | G06F 17/30392 |
| 2010/0100848 A1* | 4/2010 | Ananian | G06F 3/0482 715/834 |
| 2010/0185984 A1* | 7/2010 | Wright | G06T 11/206 715/833 |
| 2010/0228752 A1* | 9/2010 | Folting | G06F 17/246 707/758 |
| 2011/0016432 A1* | 1/2011 | Helfman | G06F 3/0482 715/843 |
| 2011/0032260 A1* | 2/2011 | Duggan | H04L 41/0604 345/440 |
| 2011/0087644 A1* | 4/2011 | Frieden | G06F 17/30144 707/706 |
| 2011/0087678 A1* | 4/2011 | Frieden | G06F 17/30867 707/749 |
| 2011/0087954 A1* | 4/2011 | Dickerman | G06F 17/246 715/219 |
| 2011/0109472 A1* | 5/2011 | Spirakis | G06Q 10/06 340/870.02 |
| 2011/0173219 A1* | 7/2011 | Bent | G06F 17/30545 707/769 |
| 2011/0320410 A1* | 12/2011 | Marum | G06F 17/30389 707/687 |
| 2012/0005045 A1* | 1/2012 | Baker | G06Q 30/0643 705/27.2 |
| 2012/0023101 A1* | 1/2012 | Heimendinger | G06F 17/30522 707/737 |
| 2012/0089633 A1* | 4/2012 | Vigneau | G06F 17/30592 707/769 |
| 2012/0109984 A1* | 5/2012 | Clark, Jr. | G06F 17/30554 707/754 |
| 2012/0179699 A1* | 7/2012 | Ward | G06F 17/30589 707/754 |
| 2012/0204122 A1* | 8/2012 | Brugler | G06F 17/10 715/771 |
| 2012/0240064 A1* | 9/2012 | Ramsay | G06T 11/00 715/762 |
| 2012/0266074 A1* | 10/2012 | Bhoovaraghavan | G06F 11/32 715/738 |
| 2013/0055146 A1* | 2/2013 | Armitage | G06F 3/0481 715/781 |
| 2013/0111320 A1* | 5/2013 | Campbell | G06F 17/245 715/212 |
| 2013/0262277 A1* | 10/2013 | Clark, Jr. | G06Q 10/00 705/30 |
| 2013/0282696 A1* | 10/2013 | John | G06F 17/30991 707/722 |
| 2013/0321285 A1* | 12/2013 | Hoyer | G06F 3/0488 345/173 |
| 2014/0059069 A1* | 2/2014 | Taft | G06F 17/30442 707/765 |
| 2014/0081906 A1* | 3/2014 | Geddam | H04L 67/1097 707/609 |
| 2014/0325444 A1* | 10/2014 | Garrison | G06F 3/0482 715/825 |
| 2015/0058092 A1* | 2/2015 | Rea | G06W 10/0639 705/7.38 |
| 2015/0066910 A1* | 3/2015 | Bleach | G06F 17/30451 707/722 |
| 2017/0123627 A1* | 5/2017 | Cristoforo | G06Q 40/04 |

OTHER PUBLICATIONS

Bruce R. Rabe, et al.; "Automatic Layout of Graphical User Interface Screens From Object Data"; U.S. Appl. No. 13/799,547, filed Mar. 13, 2013.

Bruce R. Rabe, et al.; "Proficiency-Based GUI Adaptation"; U.S. Appl. No. 13/833,356, filed Mar. 15, 2013.

* cited by examiner

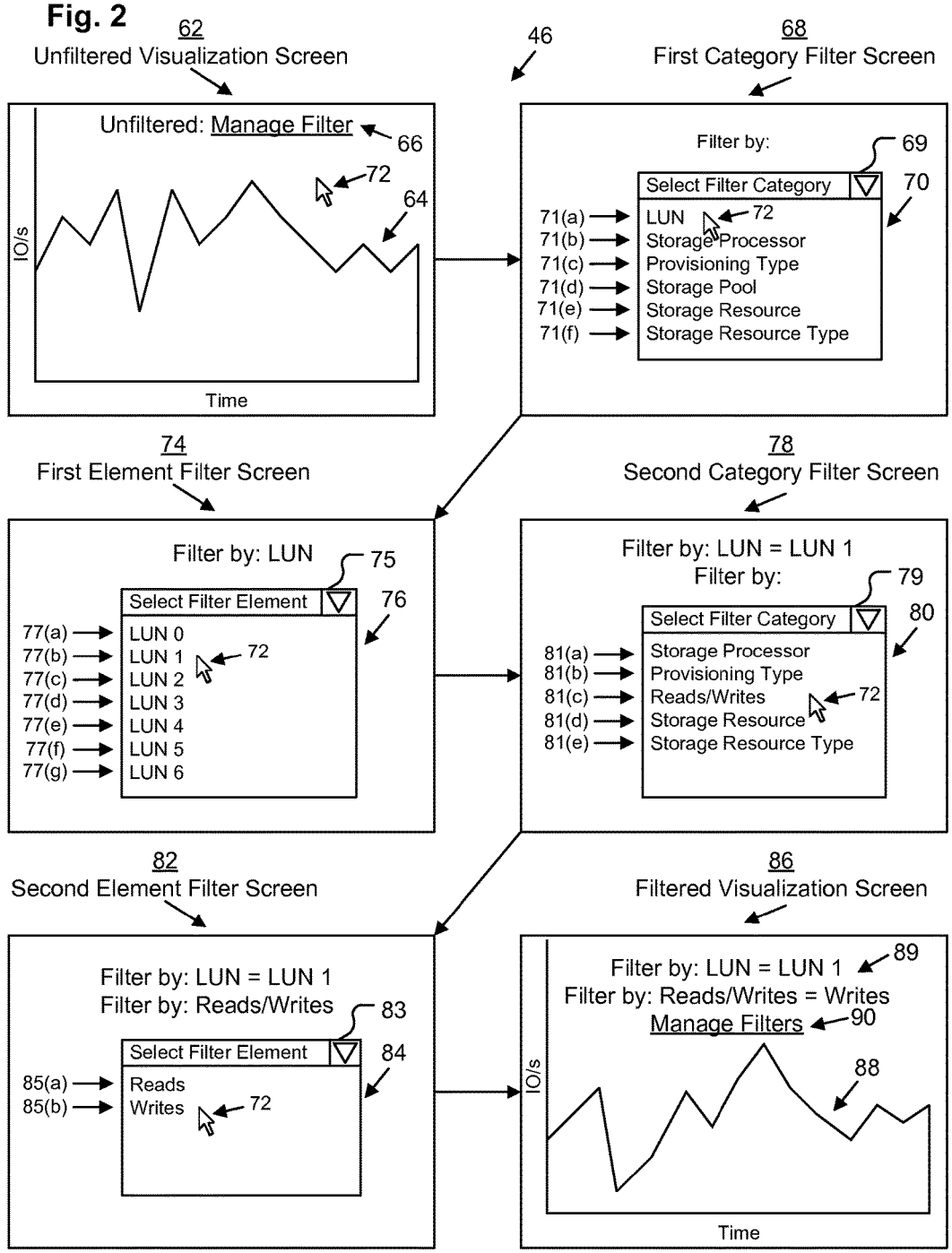

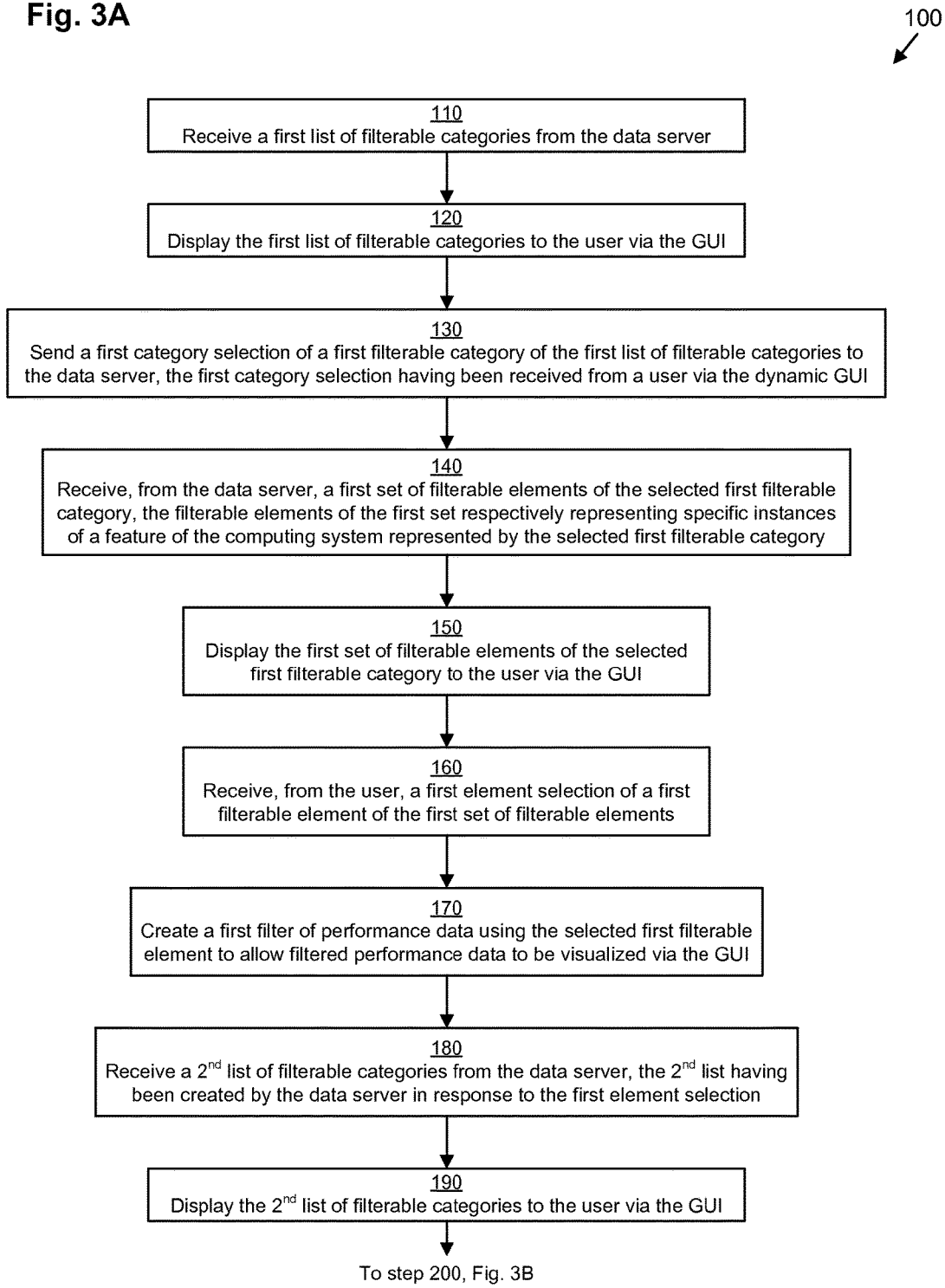

US 10,156,961 B1

DYNAMICALLY BUILDING A VISUALIZATION FILTER

BACKGROUND

Large amounts of performance data are often recorded by modern data storage systems, allowing for detailed performance metrics to be calculated and visualized. An example of a typical modern data storage system is a VNX Series data storage system produced by the EMC Corp. of Hopkinton, Mass. The performance of a data storage system (e.g., in average I/O transactions per second, percent processor utilization, megabytes transferred per second, etc.) may be tracked over time and displayed on a graph.

SUMMARY

The above-described conventional systems for filtering performance data and displaying filtered performance graphs may suffer from deficiencies. In particular, it can be difficult to construct a filter for the exact parameters that a user wishes to visualize in the context of a large and complex data storage system.

Thus, it would be desirable to alleviate these concerns by allowing a user to easily and dynamically construct a filter for performance data of a computing system (e.g., a data storage system) to allow specific filtered performance visualizations to be displayed. Thus, embodiments are directed to techniques for presenting a dynamic graphical user interface (GUI) for selecting consistent filters to be used to filter performance data for display in a visualization.

One embodiment is directed to a method of allowing a user to filter a performance data visualization using a GUI on a computing device. The method includes (a) sending a category selection of a particular filterable category of a list of filterable categories to a data server, the category selection having been received from a user via the GUI, the filterable categories representing respective categories of elements for which a computing system records regarding performance of the computing system, (b) in response to sending the category selection to the data server, receiving a set of filterable elements from the data server, the filterable elements of the set respectively representing specific instances of a feature of the computing system represented by the selected particular filterable category, (c) displaying the set of filterable elements of the selected particular filterable category to the user via the GUI, (d) after displaying the set of filterable elements, receiving, from the user, an element selection of a particular filterable element of the set of filterable elements, and (e) creating a filter of performance data of the computing system using the selected particular filterable element to allow filtered performance data to be visualized via the GUI. Other embodiments are directed to a computerized apparatus and computer program products for performing methods similar to that described above.

BRIEF DESCRIPTION OF THE DRAWINGS

The foregoing and other objects, features and advantages will be apparent from the following description of particular embodiments of the present disclosure, as illustrated in the accompanying drawings in which like reference characters refer to the same parts throughout the different views. The drawings are not necessarily to scale, emphasis instead being placed upon illustrating the principles of various embodiments of the present disclosure.

FIG. 2 depicts an example set of GUI screens.

FIGS. 3A-3B depicts an example method according to various embodiments.

DETAILED DESCRIPTION

Embodiments are directed to techniques for presenting a dynamic graphical user interface (GUI) for selecting consistent filters to be used to filter performance data for display in a visualization.

Figure 1:
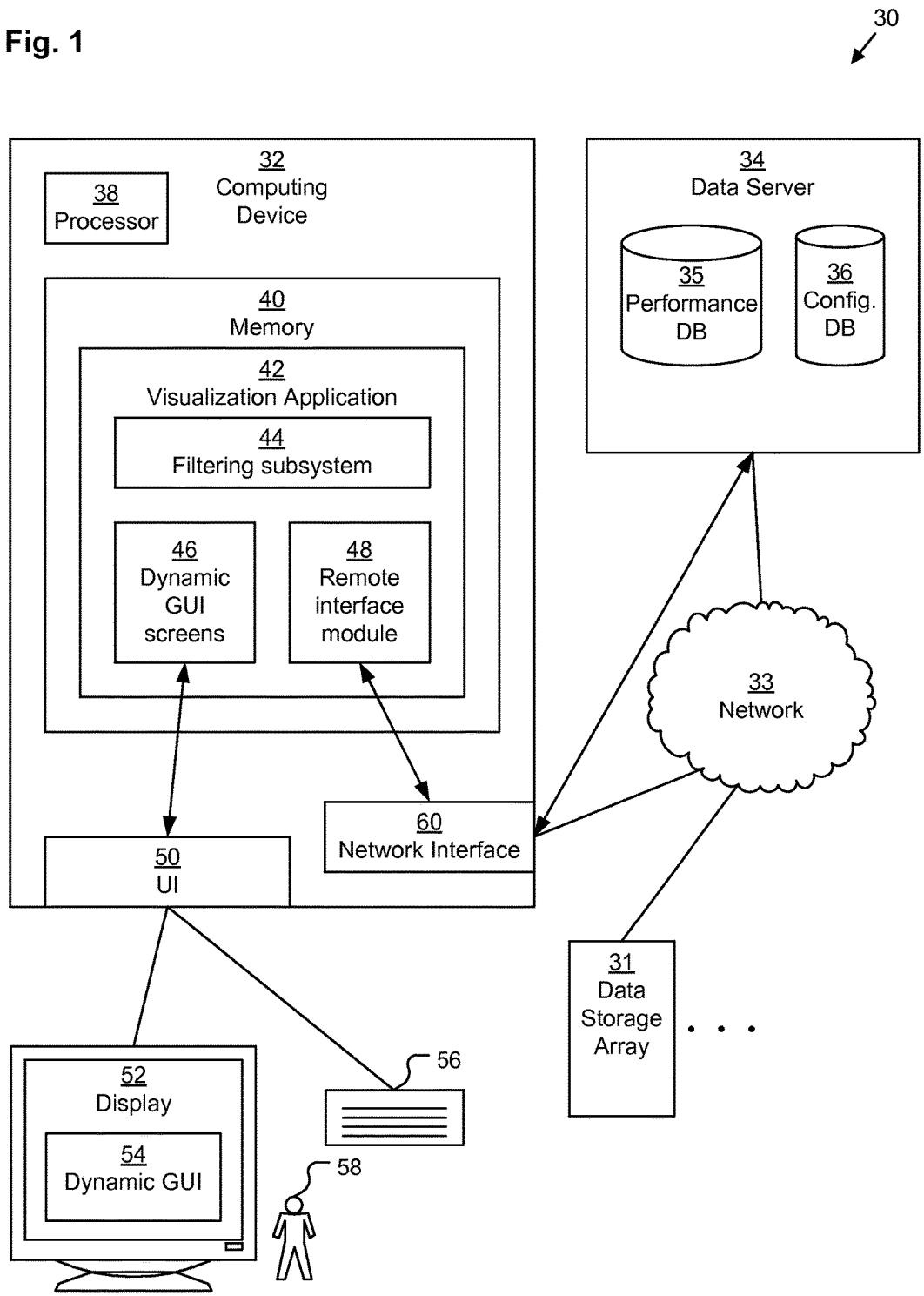
FIG. 1 depicts an example system for use in performing various embodiments.

FIG. 1 depicts an example data storage system 30. In some embodiments, system 30 may include a set of one or more data storage arrays 31, which provide the storage services of the system 30. In other embodiments, system 30 may be another kind of system other than a data storage system.

System 30 includes a computing device 32 which connects to a network 33, which allows it to access a remote data server 34 that provides performance data for the system 30 with reference to a performance database (DB) 35 stored on the remote data server 34. Performance DB 35 stores performance data for the system 30, including performance data associated with the various data storage arrays 31. Remote data server 34 also stores a system configuration DB 36. Remote data server 34 may be any kind of network-connectable computing device, such as, for example, a personal computer, a workstation computer, a server computer, an enterprise server computer, a cellular phone, a smart phone, a tablet, a laptop computer, etc., however, remote data server 34 will typically be a server computer or an enterprise server computer.

Computing device 32 may be any kind of network-connectable computing device, such as, for example, a personal computer, a workstation computer, a server computer, an enterprise server computer, a cellular phone, a smart phone, a tablet, a laptop computer, etc. Network 33 may be any kind of data communication network, such as for example the Internet, a local area network, a wide area network, a virtual private network, a cellular data network, a wireless local area network, an interconnected fabric of connections and switches, similar systems, and combinations thereof.

Computing device 32 includes a processor 38, memory 40, a user interface (UI) 50, and a network interface 60.

Processor 38 may be any kind of processor or set of processors configured to perform operations, such as, for example, a microprocessor, a multi-core microprocessor, a digital signal processor, a system on a chip, a collection of electronic circuits, a similar kind of controller, or any combination of the above.

Network interface 60 interfaces with network 33. Network interface 50 may include an Ethernet card, a cellular modem, a Wireless Fidelity (WiFi) wireless networking adapter, any other device for connecting to a network, or some combination thereof.

UI 50 allows the computing device 32 to interact with a user 58 by displaying a dynamic GUI 54 (as well as various other GUI elements) to the user 58 on a connected display 52 and receiving instructions from the user 58 via a connected input device 56. Display 52 may be any kind of display device capable of displaying a GUI, such as, for example, a cathode ray tube, a liquid crystal display, a projection device, a plasma display, or a similar device as is well-known in the art. Display 52 may also include more than one display device, each of which may use the same or different display technologies. Input device 56 may include any kind of user input devices such as, for example, a keyboard, a keypad, a mouse, a trackpad, a tracking ball, a pen-based digitizer, a stylus-based digitizer, or a similar device as is well-known in the art. Input device 56 may also include more than one user input device. In some embodiments, display 52 and user input device 56 may be combined into a single device, such as, for example, a touch-sensitive display screen. UI 50 may include one or more of a graphics adapter, a touch-based input controller, a mouse interface, a keyboard interface, a universal serial bus, or other similar devices.

Memory 40 may be any kind of digital system memory, such as, for example, RAM. Memory 40 stores programs and applications executing on processor 38 as well as data used by those programs. Memory 40 stores an operating system (not depicted) as well as various other software modules (some of which may be independent applications, while others are parts of other applications or the operating system). One application within memory 40 includes a visualization application 42. Visualization application 42, when executed by the processor 38, allows the user 58 to interact with the dynamic GUI 54 via the display 52 and input device 56 to dynamically select a set of filters to display a visualization of filtered performance data. Visualization application 42 may include various components, such as, for example, filtering subsystem 44, a set of dynamic GUI screens 46 to be displayed as dynamic GUI 54, and a remote interface module 48 for communicating with the remote data server 34 via network interface 60 and network 33. Filtering subsystem 44 is configured to, when executed by the processor 38, construct and send appropriate dynamic GUI screens 46 to be displayed within the dynamic GUI 54, receive responses from the user 58 via the input device 56 to select a particular set of filters, and cause performance data of the system 30 to be filtered and displayed within dynamic GUI 54.

Filtering subsystem 44 communicates with remote data server 34 via remote interface module 48, network interface 60, and network 33 to receive configuration information about the system 30 stored within configuration DB 36 in order to construct the dynamic GUI screens 46. In some embodiments, however, instead of performance DB 35 and configuration DB 36 residing within a remote data server 34, performance DB 35 and configuration DB 36 may reside within a data server application (not depicted) within memory 40, the remote interface module 48 serving to communicate directly with the data server application across memory 40.

In some embodiments, filtering subsystem 44 is able to filter the performance data locally by filtering performance data (received from remote data server 34 as stored in performance DB 35, or alternatively received from the data server application within memory 40) using filters set up by the user 58 in conjunction with dynamic GUI 54, while in other embodiments, filtering subsystem 44 communicates with remote data server 34 via remote interface module 48, network interface 60, and network 33 (or with data server application within memory 40 just via remote interface module 48) to send the filter information to the remote data server 34 and receive the filtered performance data back in response.

Memory 40 may include both a system memory portion for storing programs and data in active use by the processor 38 as well as a persistent storage portion (e.g., solid-state storage and/or disk-based storage) for storing programs and data even while the computing device 32 is powered off. The operating system and the applications (e.g., virtualization application 42) are typically stored both in system memory and in persistent storage so that they may be loaded into system memory from persistent storage upon a system restart. Applications (e.g., virtualization application 42), when stored in non-transient form either in system memory or in persistent storage, form a computer program product. The processor 38 running one or more of these applications (e.g., virtualization application 42) thus forms a specialized circuit constructed and arranged to carry out the various processes described herein.

FIG. 2 depicts an example set of GUI screens 46 for display within dynamic GUI 54. As depicted, the dynamic set of GUI screens 46 includes GUI screens 62, 68, 74, 78, 82, 86. Details and operation of these screens will be described in further detail in conjunction with FIGS. 3A-3B.

Figure 3B:
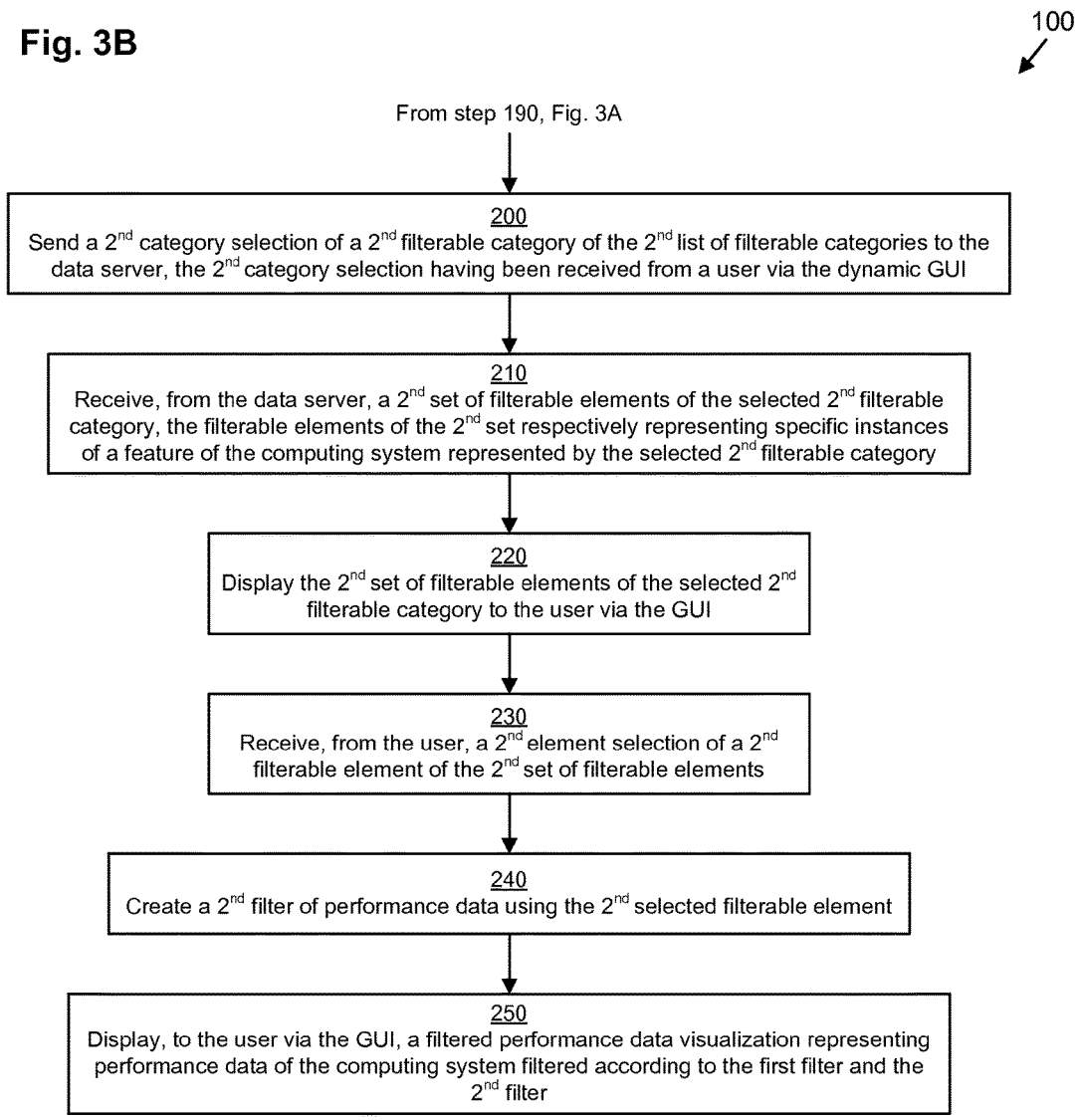

FIGS. 3A-3B illustrate, as method 100, the operation of visualization application 42 on computing device 32 for dynamically selecting and applying filters to create a visualization of filtered performance data. It should be understood that any time a piece of software, such as, for example, visualization application 42, is described as performing a method, process, step, or function, in actuality what is meant is that a computing device (e.g., computing device 32) on which that piece of software is running performs the method, process, step, or function when executing that piece of software on its processor (e.g., processor 38). It should also be understood that, in some embodiments, instead of processor 38 executing code of visualization application 42, specialized circuitry of the computing device 32 operates to perform the method, process, step, or function directly in hardware.

Preliminary to method 100, in some embodiments, visualization application 42 displays unfiltered visualization screen 62 (which is one of the dynamic GUI screens 46) within the dynamic GUI 54 of the display 52, which depicts unfiltered performance data on an unfiltered graph 64 or other kind of visualization (e.g., a chart or table). As depicted, unfiltered graph 64 plots aggregated I/O transactions per second across the entire system 30 against time. It should be understood that the term "aggregated" as used within this Specification means a sum or average or weighted average or a combined ratio. Thus, in one example, unfiltered graph 64 plots I/O transactions per second summed together from the various storage processors of the various data storage arrays 31 of the system 30. Other sorts of aggregation may also be used instead. In addition, other performance metrics may be used instead of I/O transactions per second (e.g., storage processor cache throughput, storage processor cache dirty ratio, LUN response time, etc.). Unfiltered visualization screen 62 also includes a filter management link 66. When the user 58 operates a cursor 72 (e.g., using a mouse or other input device 56) to click on (or otherwise select) filter management link 66, method 100 is triggered.

In step 110, visualization application 42 receives a first list 70 (see FIG. 2) of filterable categories 71 from the data server 34. In step 120, visualization application 42 displays the first list 70 of filterable categories 71 (depicted as filterable categories 71(*a*), 71(*b*), 71(*c*), 71(*d*), 71(*e*), 71(*f*), although this is by way of example only) to the user 58 via the dynamic GUI 54. The filterable categories 71 each represent categories of elements against which the particular performance metric is recorded. Thus, for example, for the disk throughput metric (I/O transactions per second), I/O transactions per second are recorded periodically against each LUN, storage processor, storage resource, and storage pool of the data storage system 30, and results are also broken down against provisioning type and storage resource type. In addition, in some embodiments, there may be additional filterable categories for which the performance metric is recorded but which are not included within the first list 70 of filterable categories 71. For example, the disk throughput metric may also be broken down separately against read and write operations, but the read/write filterable category (see 81(c) below) may not be displayed with the first list 70 of filterable categories 71 for purposes of clarity of presentation, etc. Thus, as depicted for the disk throughput metric, the filterable categories 71 of the first list 70 include LUN, Storage Processor, Provisioning Type, Storage Pool, Storage Resource, and Storage Resource Type, allowing the user 58 to create a filter using one of these filterable categories 71 by clicking on one of them using cursor 72. As depicted, since the unfiltered graph 64 plots I/O transactions against time, the particular filterable categories 71 displayed (i.e., LUN, Storage Processor, Provisioning Type, Storage Pool, Storage Resource, and Storage Resource Type) are considered relevant. In other arrangements, for other raw sets of unfiltered performance data or for other systems 30, different filterable categories 71 may be relevant. In particular, different performance metrics may have different associated lists 70 of filterable categories 71. For example, the storage processor cache throughput metric (which measures the number of I/O transactions passing through the storage processor cache) may include the following three filterable categories 71: Storage Processor, Reads/Writes, and Hit/Miss.

In some embodiments, filtering subsystem 44 initiates step 110 by sending a request (e.g., a representational state transfer or REST based request) to the remote data server 34 via remote interface module 48, network interface 60, and network 33, upon which the remote data server 34 determines the first list 70 with reference to the configuration DB 36 and then sends a response (e.g., a REST response) back to the filtering subsystem 44 via network 33, network interface 60, and remote interface module 48. In other embodiments, the request is sent within memory 40 directly to the data server application via remote interface module 48, and the response is similarly received directly from within memory 40 from the data server application via remote interface module 48.

In accomplishing step 120, filtering subsystem 44 creates first category filter screen 68 within dynamic GUI screens 46, the first category filter screen 68 having a selection box 69 that displays the first list 70, and filtering subsystem 44 then displays the created first category filter screen 68 as part of the dynamic GUI 54 on display 52. As depicted, when user 58 clicks, using cursor 72, on the LUN filterable category 71(a), for example, filtering subsystem 44 responds, in step 130, by selecting that first particular filterable category 71(a) and sending an indication of that first particular filterable category 71(a) to the data server 34 (e.g., using a REST request, as above).

In step 140, filtering subsystem 44 receives a first set 76 (see FIG. 2) of filterable elements 77 from data server 34 (e.g., via a REST response, as above). In step 150, filtering subsystem 44 displays the first set 76 of filterable elements 77 (depicted as filterable elements 77(a), 77(b), 77(c), 77(d), 77(e), 77(f), 77(g), although this is by way of example only) within a selection box 75 on first element filter screen 74. The filterable elements 77 each represent instances of the selected first filterable category 71(a). Thus, as depicted, the filterable elements 77 of the first set 76 include LUN 0, LUN 1, LUN 2, LUN 3, LUN 4, LUN 5, and LUN 6, allowing the user 58 to create a filter based on the selected first filterable category 71(a) by clicking (step 160) on one of the filterable elements 77 using cursor 72.

As depicted, since the selected first filterable category 71(a) is the LUN category (representing logical unit numbers of logical disks of the system 30), the particular filterable elements 77 displayed (i.e., LUN 0, LUN 1, LUN 2, LUN 3, LUN 4, LUN 5, and LUN 6) are considered relevant because those are the LUNs present within the system 30, the performance data being based on an aggregate of the performance of those LUNs. In other arrangements, for other selected filterable categories 71 or for different systems having different elements installed within the selected first filterable category 71(a), different filterable elements 77 may be relevant.

Just prior to step 140, the data server 34 determines the first set 77 with reference to the configuration DB 36 and then sends the response (e.g., a REST response, as above) back to the filtering subsystem 44 to be received in step 140.

As depicted, when user 58 clicks, using cursor 72, on the LUN 1 filterable element 77(b) (step 160), for example, the selected first filterable element 77(b) completes the definition of the first filter, allowing the filtering subsystem 44 to generate (step 170) the first filter with a form "LUN=LUN 1." Subsequently, visualization module 42 responds by displaying a confirmation screen (not depicted), listing the first filter, and allowing the user 58 to either apply the first filter to the performance data or to select a second filter.

Selecting the second filter being the more interesting case, upon the user 58 choosing the option to select a second filter, operation proceeds to step 180, in which filtering subsystem 44 receives a second list 80 of filterable categories 81 from data server 34 (e.g., via a REST response, as above). In step 190, filtering subsystem 44 displays the second list 80 of filterable categories 81 (depicted as filterable categories 81(a), 81(b), 81(c), 81(d), 81(e), although this is by way of example only) within a selection box 79 on second category filter screen 68. The filterable categories 81 each represent categories of elements against which the particular performance metric is recorded, but the particular filterable categories 81 within the second list 80 may differ from the filterable categories 71 within the first list 70 in various ways. As depicted, because a particular LUN (i.e., LUN 1) has already been selected as part of the first filter, there is no longer any need to allow for another LUN filter (the filters being applied in a conjunctive manner, although, in an alternative embodiment, in which the filters are applied in a disjunctive manner, another LUN filter may be applied, so the LUN filterable category 71(a) may remain), so the LUN filterable category 71(a) is removed from the first list 70 to generate the second list 80. In addition, as depicted, because a particular LUN (i.e., LUN 1) has already been selected as part of the first filter, the Storage Pool filterable category 71(d) is also removed. This is because a storage pool contains (i.e., is a container of) a set of LUNs, so adding a filter based on storage pool would be superfluous in a conjunctive filtering situation since no possible selection of storage pool together with the selection of LUN could modify the data over using a single filter based solely on the LUN. In addition, as depicted, an additional filterable category 81(c) for Reads/Writes has been added. This additional filterable category 81(c) has been added because although it could have been within the original first list 70, in order to avoid overcrowding the first list 70 with too many choices, certain less-frequently selected options may be omitted until the length of the list decreases in the second list 80.

Just prior to step 180, the data server 34 determines the second list 80 with reference to the configuration DB 36 and then sends the response (e.g., a REST response, as above) back to the filtering subsystem 44 to be received in step 180.

Thus, as depicted, the filterable categories 81 of the second list 70 include Storage Processor, Provisioning Type, Reads/Writes, Storage Resource, and Storage Resource Type, allowing the user 58 to create a second filter using one of these filterable categories 81 by clicking on one of them using cursor 72 (step 200). As depicted, since the unfiltered graph 64 plots I/O transactions against time, the particular filterable categories 81 displayed (i.e., Storage Processor, Provisioning Type, Reads/Writes, Storage Resource, and Storage Resource Type) are considered relevant and are not excluded based upon the above-mentioned concerns. In other arrangements, for other raw sets of unfiltered performance data or for other systems 30 with different configurations, different filterable categories 81 may be relevant.

As depicted, when user 58 clicks, using cursor 72, for example, on the Reads/Writes filterable category 81(c), filtering subsystem 44 responds, in step 200, by sending a second category selection (indicating the selected Reads/Writes filterable category 81(c)) to the data server 34 (e.g., using a REST request, as above).

In step 210, filtering subsystem 44 receives a second set 84 (see FIG. 2) of filterable elements 85 from data server 34 (e.g., via a REST response, as above). In step 220, filtering subsystem 44 displays the second set 84 of filterable elements 85 (depicted as filterable elements 85(a), 85(b), although this is by way of example only) within a selection box 83 on second element filter screen 82. The filterable elements 85 each represent instances of the selected second filterable category 81(c). Thus, as depicted, the filterable elements 85 of the second set 84 include Reads and Writes, allowing the user 58 to create a second filter based on the selected second filterable category 81(c) by clicking (step 230) on one of the filterable elements 85 using cursor 72.

As depicted, since the selected second filterable category 81(c) is the Reads/Writes category (representing a choice between transaction types performed within the system 30), the particular filterable elements 85 displayed (i.e., Reads and Writes) are considered relevant because those are the possible transaction types in the context of the system 30. In other arrangements, for other selected filterable categories 81 or for different systems having different elements within the selected second filterable category 81(c), different filterable elements 85 may be relevant.

Just prior to step 210, the data server 34 determines the second set 84 with reference to the configuration DB 36 and then sends the response (e.g., a REST response, as above) back to the filtering subsystem 44 to be received in step 210.

As depicted, when user 58 clicks, using cursor 72, on the Writes filterable element 85(b) (step 230), for example, the selected second filterable element 85(b) completes the definition of the second filter, allowing the filtering subsystem 44 to generate (step 240) the second filter with a form "Reads/Writes=Writes." Subsequently, visualization module 42 responds by displaying filtered visualization screen 86 (step 250). Filtered visualization screen 86 lists the set of filters 89 (e.g., "Filter by: LUN=LUN 1; Filter by: Reads/Writes=Writes"), a filter management link 90 (to allow additional filters to be added or to remove filters), and a visualization of filtered performance data, such as chart 88.

In some embodiments, filtering subsystem 44 generates chart 88 by sending a request (e.g., a REST based request) to the remote data server 34 or the data server application via remote interface module 48, allowing the data server 34 to respond with performance data from the performance DB 35 that allows the filtering subsystem 44 to generate the chart 88. In some of these embodiments, the data server 34 filters the performance data from the performance DB 35 using the selected filters and only sends the filtered performance data back to the filtering subsystem 44. In other of these embodiments, the data server 34 does not filter the performance data from the performance DB 35 using the selected filters, thereby sending all performance data from the performance DB 35 to the filtering subsystem 44, the filtering subsystem 44 being responsible to apply the selected filters locally to the received performance data to generate the filtered performance data locally on the computing device 32.

Thus, techniques have been described for presenting a dynamic GUI 54 for selecting consistent filters to be used to filter performance data for display in a visualization 88.

While various embodiments of the present disclosure have been particularly shown and described, it will be understood by those skilled in the art that various changes in form and details may be made therein without departing from the spirit and scope of the present disclosure as defined by the appended claims.

For example, although various embodiments have been described as being methods, software embodying these methods is also included. Thus, one embodiment includes a tangible non-transitory computer-readable storage medium (such as, for example, a hard disk, a floppy disk, an optical disk, computer memory, flash memory, etc.) programmed with instructions, which, when performed by a computer or a set of computers, cause one or more of the methods described in various embodiments to be performed. Another embodiment includes a computer which is programmed to perform one or more of the methods described in various embodiments.

Furthermore, it should be understood that all embodiments which have been described may be combined in all possible combinations with each other, except to the extent that such combinations have been explicitly excluded.

Finally, even if a technique, method, apparatus, or other concept is specifically labeled as "conventional," Applicants make no admission that such technique, method, apparatus, or other concept is actually prior art under 35 U.S.C. § 102 or 35 U.S.C. § 103, such determination being a legal determination that depends upon many factors, not all of which are known to Applicants at this time.

What is claimed is:

1. A method, performed by a computing device, of dynamically constructing and displaying a filtered performance visualization for a distributed data storage system using a graphical user interface (GUI) on the computing device, the method comprising:

receiving, from a remote data server, a set of data points representing performance of the distributed data storage system, the set of data points including data points that represent performance of each data storage array of a set of data storage arrays of the distributed data storage system at a sequence of time periods, the performance of any given data storage array at a given time period being a measure of Input/Output (I/O) operations per second performed by that data storage array during that time period;

displaying, using the GUI, an unfiltered graph of the set of data points in an aggregated manner plotted against time by:

for each time period, calculating an aggregated I/O operations per second measurement of the distributed data storage system by summing together all the measures of I/O operations per second of every data storage array of the set of data storage arrays; and displaying a graph of the calculated aggregated I/O operations per second measurement of the distributed data storage system against time;

receiving a list of filterable categories from the remote data server, the filterable categories representing respective categories of elements for which the distributed data storage system records regarding performance of the distributed data storage system;

displaying the list of filterable categories to the user via the GUI;

subsequent to displaying the list of filterable categories to the user via the GUI, receiving a category selection of a particular filterable category of the received list of filterable categories from a user via the GUI;

sending the category selection to the remote data server;

in response to sending the category selection to the remote data server, receiving a set of filterable elements from the remote data server, the filterable elements of the set respectively representing specific instances of a feature of the distributed data storage system represented by the selected particular filterable category;

displaying the set of filterable elements of the selected particular filterable category to the user via the GUI;

after displaying the set of filterable elements, receiving, from the user, an element selection of a particular filterable element of the set of filterable elements;

receiving another list of filterable categories from the remote data server, the other list of filterable categories being different than the list of filterable categories by having the selected particular filterable category removed, the other list of filterable categories having been created by the remote data server in response to the element selection;

displaying the other list of filterable categories to the user via the GUI, wherein displaying the other list includes displaying the other list of filterable elements while refraining from displaying the selected particular filterable category as part of the other list;

after displaying the other list of filterable categories, receiving another category selection of another particular filterable category of the other list of filterable categories from the user via the GUI;

sending the other category selection to the remote data server;

in response to sending the other category selection to the remote data server, receiving another set of filterable elements from the remote data server, the filterable elements of the other set respectively representing specific instances of another feature of the distributed data storage system represented by the other selected particular filterable category;

displaying the other set of filterable elements of the other selected particular filterable category to the user via the GUI;

after displaying the other set of filterable elements, receiving, from the user, another element selection of another particular filterable element of the other set of filterable elements;

filtering performance data of the distributed data storage system by removing data points from the set of data points that do not represent both the selected particular filterable element and the other selected particular filterable element, yielding a filtered set of data points; and displaying, using the GUI, a graph of the filtered set of data points in an aggregated manner plotted against time by:

for each time period, calculating a filtered aggregated I/O operations per second measurement of the distributed data storage system by summing together all the measures of I/O operations per second of every data storage array of the set of data storage arrays, disregarding the removed data points; and displaying a graph of the calculated filtered aggregated I/O operations per second measurement of the distributed data storage system against time;

wherein communicating with the remote data server is done using a representational state transfer (REST) architecture.

2. The method of claim 1 wherein receiving the other list of filterable categories from the remote data server includes receiving the list of filterable categories further having all filterable categories from the list which are containers of elements of a type defined by the selected particular filterable category removed.

3. The method of claim 1 wherein receiving the other list of filterable categories from the remote data server includes receiving the list of filterable categories further having an additional filterable category, the additional filterable category not being found within the list of filterable categories.

4. A computer program product comprising a non-transitory computer-readable medium storing instructions, which, when executed by a computing device, cause the computing device to perform the operations of:

receiving, from a remote data server, a set of data points representing performance of a distributed data storage system, the set of data points including data points that represent performance of each data storage array of a set of data storage arrays of the distributed data storage system at a sequence of time periods, the performance of any given data storage array at a given time period being a measure of Input/Output (I/O) operations per second performed by that data storage array during that time period;

displaying, using a graphical user interface (GUI), an unfiltered graph of the set of data points in an aggregated manner plotted against time by:

for each time period, calculating an aggregated I/O operations per second measurement of the distributed data storage system by summing together all the measures of I/O operations per second of every data storage array of the set of data storage arrays; and displaying a graph of the calculated aggregated I/O operations per second measurement of the distributed data storage system against time;

receiving a list of filterable categories from the remote data server, the filterable categories representing respective categories of elements for which the distributed data storage system records regarding performance of the distributed data storage system;

displaying the list of filterable categories to the user via the GUI;

subsequent to displaying the list of filterable categories to the user via the GUI, receiving a category selection of a particular filterable category of the received list of filterable categories from a user via the GUI;

sending the category selection to the remote data server;

in response to sending the category selection to the remote data server, receiving a set of filterable elements from the remote data server, the filterable elements of the set respectively representing specific instances of a feature of the distributed data storage system represented by the selected particular filterable category;

displaying the set of filterable elements of the selected particular filterable category to the user via the GUI;

after displaying the set of filterable elements, receiving, from the user, an element selection of a particular filterable element of the set of filterable elements;

receiving another list of filterable categories from the remote data server, the other list of filterable categories being different than the list of filterable categories by having the selected particular filterable category removed, the other list of filterable categories having been created by the remote data server in response to the element selection;

displaying the other list of filterable categories to the user via the GUI, wherein displaying the other list includes displaying the other list of filterable elements while refraining from displaying the selected particular filterable category as part of the other list;

after displaying the other list of filterable categories, receiving another category selection of another particular filterable category of the other list of filterable categories from the user via the GUI;

sending the other category selection to the remote data server;

in response to sending the other category selection to the remote data server, receiving another set of filterable elements from the remote data server, the filterable elements of the other set respectively representing specific instances of another feature of the distributed data storage system represented by the other selected particular filterable category;

displaying the other set of filterable elements of the other selected particular filterable category to the user via the GUI;

after displaying the other set of filterable elements, receiving, from the user, another element selection of another particular filterable element of the other set of filterable elements;

filtering performance data of the distributed data storage system by removing data points from the set of data points that do not represent both the selected particular filterable element and the other selected particular filterable element, yielding a filtered set of data points; and displaying, using the GUI, a graph of the filtered set of data points in an aggregated manner plotted against time by:

for each time period, calculating a filtered aggregated I/O operations per second measurement of the distributed data storage system by summing together all the measures of I/O operations per second of every data storage array of the set of data storage arrays, disregarding the removed data points; and displaying a graph of the calculated filtered aggregated I/O operations per second measurement of the distributed data storage system against time;

wherein communicating with the remote data server is done using a representational state transfer (REST) architecture.

5. The computer program product of claim 4 wherein receiving the other list of filterable categories from the remote data server further includes receiving the list of filterable categories having all filterable categories from the list which are containers of elements of a type defined by the selected particular filterable category removed.

6. The computer program product of claim 4 wherein receiving the other list of filterable categories from the remote data server includes receiving the list of filterable categories having an additional filterable category, the additional filterable category not being found within the list of filterable categories.

7. An apparatus comprising:
memory;
a graphical user interface (GUI); and
a controller, the controller being configured to perform the following operations:

receiving, from a remote data server, a set of data points representing performance of a distributed data storage system, the set of data points including data points that represent performance of each data storage array of a set of data storage arrays of the distributed data storage system at a sequence of time periods, the performance of any given data storage array at a given time period being a measure of Input/Output (I/O) operations per second performed by that data storage array during that time period;

displaying, using the GUI, an unfiltered graph of the set of data points in an aggregated manner plotted against time by:

for each time period, calculating an aggregated I/O operations per second measurement of the distributed data storage system by summing together all the measures of I/O operations per second of every data storage array of the set of data storage arrays; and displaying a graph of the calculated aggregated I/O operations per second measurement of the distributed data storage system against time;

receiving a list of filterable categories from the remote data server, the filterable categories representing respective categories of elements for which the distributed data storage system records regarding performance of the distributed data storage system;

displaying the list of filterable categories to the user via the GUI;

subsequent to displaying the list of filterable categories to the user via the GUI, receiving a category selection of a particular filterable category of the received list of filterable categories from a user via the GUI;

sending the category selection to the remote data server;

in response to sending the category selection to the remote data server, receiving a set of filterable elements from the remote data server, the filterable elements of the set respectively representing specific instances of a feature of the distributed data storage system represented by the selected particular filterable category;

displaying the set of filterable elements of the selected particular filterable category to the user via the GUI;

after displaying the set of filterable elements, receiving, from the user, an element selection of a particular filterable element of the set of filterable elements;

receiving another list of filterable categories from the remote data server, the other list of filterable categories being different than the list of filterable categories by having the selected particular filterable category removed, the other list of filterable categories having been created by the remote data server in response to the element selection;

displaying the other list of filterable categories to the user via the GUI, wherein displaying the other list includes displaying the other list of filterable elements while refraining from displaying the selected particular filterable category as part of the other list;

after displaying the other list of filterable categories, receiving another category selection of another particular filterable category of the other list of filterable categories from the user via the GUI;

sending the other category selection to the remote data server;

in response to sending the other category selection to the remote data server, receiving another set of filterable elements from the remote data server, the filterable elements of the other set respectively representing specific instances of another feature of the distributed data storage system represented by the other selected particular filterable category;

displaying the other set of filterable elements of the other selected particular filterable category to the user via the GUI;

after displaying the other set of filterable elements, receiving, from the user, another element selection of another particular filterable element of the other set of filterable elements;

filtering performance data of the distributed data storage system by removing data points from the set of data points that do not represent both the selected particular filterable element and the other selected particular filterable element, yielding a filtered set of data points; and displaying, using the GUI, a graph of the filtered set of data points in an aggregated manner plotted against time by:

for each time period, calculating a filtered aggregated I/O operations per second measurement of the distributed data storage system by summing together all the measures of I/O operations per second of every data storage array of the set of data storage arrays, disregarding the removed data points; and displaying a graph of the calculated filtered aggregated I/O operations per second measurement of the distributed data storage system against time;

wherein communicating with the remote data server is done using a representational state transfer (REST) architecture.

8. The method of claim 1 wherein:

sending the category selection to the remote data server includes sending the category selection to the remote data server over a network connection.

* * * * *